US011439595B2

(12) United States Patent
Nowak et al.

(10) Patent No.: US 11,439,595 B2
(45) Date of Patent: Sep. 13, 2022

(54) IMMEDIATE RELEASE FORMULATIONS OF CANNABINOIDS

(71) Applicant: Glatt GmbH, Binzen (DE)

(72) Inventors: Reinhard Nowak, Lörrach (DE); Zafar Iqbal, Sloatsburg, NY (US); Mohammed Taleb, Nanuet, NY (US)

(73) Assignee: Glatt GmbH, Binzen (DE)

( * ) Notice: Subject to any disclaimer, the term of this patent is extended or adjusted under 35 U.S.C. 154(b) by 176 days.

(21) Appl. No.: 16/513,154

(22) Filed: Jul. 16, 2019

(65) Prior Publication Data

US 2020/0061022 A1 Feb. 27, 2020

Related U.S. Application Data

(60) Provisional application No. 62/700,107, filed on Jul. 18, 2018.

(51) Int. Cl.

| | | |
|---|---|---|
| *A61K 9/16* | (2006.01) |
| *A61K 31/05* | (2006.01) |
| *A61K 31/352* | (2006.01) |
| *A61K 9/00* | (2006.01) |
| *A61K 9/48* | (2006.01) |
| *A61K 36/185* | (2006.01) |

(52) U.S. Cl.
CPC .......... *A61K 9/1652* (2013.01); *A61K 9/0053* (2013.01); *A61K 9/0056* (2013.01); *A61K 9/1611* (2013.01); *A61K 9/1617* (2013.01); *A61K 9/1623* (2013.01); *A61K 9/1635* (2013.01); *A61K 9/1658* (2013.01); *A61K 9/1664* (2013.01); *A61K 9/1676* (2013.01); *A61K 9/48* (2013.01); *A61K 31/05* (2013.01); *A61K 31/352* (2013.01); *A61K 36/185* (2013.01)

(58) Field of Classification Search
CPC ... A61K 31/352; A61K 9/0053; A61K 9/1652
See application file for complete search history.

(56) References Cited

U.S. PATENT DOCUMENTS

| | | | |
|---|---|---|---|
| 5,662,932 | A | 9/1997 | Amselem et al. |
| 5,891,496 | A | 4/1999 | Hannah et al. |
| 6,328,992 | B1 | 12/2001 | Brooke et al. |
| 6,354,728 | B1 | 3/2002 | Bretschneider et al. |
| 6,380,175 | B1 | 4/2002 | Hussain et al. |
| 6,383,513 | B1 | 5/2002 | Watts et al. |
| 6,509,005 | B1 | 1/2003 | Peart et al. |
| 6,713,048 | B2 | 3/2004 | Peart et al. |
| 6,946,150 | B2 | 9/2005 | Whittle |
| 7,993,595 | B2 | 8/2011 | Jacob et al. |
| 8,597,685 | B2 | 12/2013 | Jacob et al. |
| 10,179,109 | B2 | 1/2019 | Bosse et al. |
| 2012/0231083 | A1 | 9/2012 | Carley et al. |
| 2016/0022627 | A2 | 1/2016 | Smith |
| 2016/0051480 | A1 | 2/2016 | Taha |
| 2018/0085308 | A1 | 3/2018 | Renwick et al. |
| 2018/0214412 | A1* | 8/2018 | Renwick et al. |
| 2018/0264013 | A1 | 9/2018 | Dill |
| 2018/0325861 | A1 | 11/2018 | Domb et al. |

FOREIGN PATENT DOCUMENTS

| | | |
|---|---|---|
| CN | 1886117 | 12/2006 |
| EP | 1125629 | 8/2001 |
| EP | 1325775 | 7/2003 |
| EP | 1361864 | 12/2013 |
| WO | WO 2002/064109 | 9/2002 |
| WO | WO 04052607 | 6/2004 |
| WO | WO 2008/027442 | 3/2008 |
| WO | WO 2016/144376 | 9/2016 |
| WO | WO 2016/205923 | 12/2016 |
| WO | WO 2017/072762 | 5/2017 |
| WO | WO 2018/035030 | 2/2018 |
| WO | WO 2018/071581 | 4/2018 |
| WO | WO 2019/159174 | 8/2019 |

OTHER PUBLICATIONS

U.S. Non-Final Office Action issued for corresponding U.S. Appl. No. 16/513,068 dated May 14, 2020.
Non-Final Office Action for U.S. Appl. No. 16/512,967 dated Jul. 24, 2020.
Written Opinion of the International Search Authority for Application No. PCT/IB2019/000847 dated Jan. 20, 2020.
International Search Report for Application No. PCT/IB2019/000847 dated Jan. 20, 2020.
Written Opinion of the International Search Authority for Application No. PCT/IB2019/0000857 dated Jan. 21, 2020.
International Search Report for Application No. PCT/IB2019/000857 dated Jan. 21, 2020.
Written Opinion of the International Search Authority for Application No. PCT/IB2019/000860 dated Jan. 20, 2020.
International Search Report for Application No. PCT/IB2019/000860 dated Jan. 20, 2020.
Non-Final Office Action for U.S. Appl. No. 16/513,068 dated Oct. 8, 2020.

(Continued)

*Primary Examiner* — Kevin E Weddington
(74) *Attorney, Agent, or Firm* — Haug Partners LLP

(57) ABSTRACT

Compositions for the immediate release of one or more cannabinoids, in which the compositions comprise a population of particles. Each particle may comprise the one or more cannabinoids and one or more intra-granule excipients. Alternatively, each particle may comprise the one or more cannabinoids and a porous bead core. The composition may be prepared by a method that involves combining the one or more cannabinoids with the one or more intra-granule excipients, and then granulating the combination, such as through fluid bed granulation, shear-induced wet granulation, or spray granulation. The composition may also be prepared by a method that involves mixing the one or more cannabinoids with a population of porous bead cores.

8 Claims, 9 Drawing Sheets

(56) References Cited

OTHER PUBLICATIONS

International Search Report for Application No. PCT/IB2019/000840 dated Jan. 3, 2020.
Written Opinion of the International Search Authority for Application No. PCT/IB2019/000840 dated Jan. 3, 2020.
Parker, W, 2009, Alcohol-containing pharmaceuticals, The American Journal of Drug and Alcohol Abuse, vol. 9, 195-209; screenshot from https ://pubmed.ncbi.nlm.nih.gov/7171081 / (Year: 2009).
Mydayis, "How Mydayis works", 2020, screenshot of https://www.mydayis.com/adhd-treatment/how-it-works (Year: 2020).
Non-Final Office Action for corresponding U.S. Appl. No. 16/513,068 dated Nov. 9, 2021.

* cited by examiner

IMMEDIATE RELEASE FORMULATIONS OF CANNABINOIDS

FIELD OF INVENTION

The present invention relates to an immediate release, multiparticulate drug delivery platform for the oral administration of one or more cannabinoids. The drug delivery system of the present invention achieves a targeted pharmacokinetic profile and provides a uniform drug distribution in the gastrointestinal tract with precisely-calculated dosing necessary for various therapeutic indications. The delivery system of the present invention can be administered as capsules, tablets, sprinkles, or a stick pack for convenience in administration and handling.

BACKGROUND OF THE INVENTION

Cannabis, the plant genus that includes both hemp and marijuana, possesses many medicinal and psychoactive properties that reportedly alleviate a wide range of symptoms experienced in connection with serious medical conditions, while providing safer and fewer serious side effects than most current prescription drugs. For example, cannabis has been used to combat symptoms associated with cancer, anorexia, AIDS, chronic pain, muscle spasticity, glaucoma, arthritis, migraine, and many other illnesses.

Cannabinoids are a class of diverse chemical compounds originating from the cannabis plant that act on cannabinoid receptors, which repress neurotransmitter release in the brain. Δ9-tetrahydrocannabinol (THC) and cannabidiol (CBD) are the two most prominent cannabinoids found in Cannabis. While there are over 100 different cannabinoids so far identified in Cannabis by scientists, CBD and THC are by far the most extensively studied and best understood. CBD and THC both interact with the body's endocannabinoid system, a vital signaling system responsible for regulating a wide array of functions.

THC is a psychotropic chemical derived from marijuana that acts on the body's cannabinoid receptors and resembles chemicals naturally produced by the body. THC is a psychoactive that activates the CB1 and CB2 receptors and affects perception, mood, consciousness, cognition, and behavior. In medicinal application, THC has the properties of an analgesic and an appetite stimulant. THC has also been reported to create a state of relaxation and well-being, induce sleep, and cause a state of euphoria. These effects have been used to treat a variety of health issues, such as pain, inflammation, nausea, sleep apnea, and stress disorders. Additionally, THC has been shown to fight the side effects and symptoms of chemotherapy, multiple sclerosis, glaucoma, AIDS, and spinal injuries.

Currently, there are only three drug products approved by the Food and Drug Administration (FDA) for THC: Marinol®, Syndros®, and Cesamet®. Marinol® and Syndros® both contain dronabinol, a synthetic THC that is insoluble in water and has a pKA of 10.6. Marinol® is available as soft gelatin capsules in dosage strengths of 2.5 mg, 5 mg, and 10 mg, and Syndros® is available as an oral solution (5 mg/ml). Both Marinol® and Syndros® are indicated for the treatment of anorexia associated with weight loss in patients with AIDS and for the treatment of nausea and vomiting associated with cancer chemotherapy in patients who have failed to respond adequately to conventional antiemetic treatments.

Cesamet® contains nabilone, a synthetic cannabinoid that is chemically similar to THC. As a raw material, nabilone is a white to off-white polymorphic crystalline powder. In aqueous media, the solubility of nabilone is less than 0.5 mg/L, with pH values ranging from 1.2 to 7.0. Cesamet® is available as a powder-filled capsule (1 mg/capsule) for oral administration and is indicated for the treatment of the nausea and vomiting associated with cancer chemotherapy in patients who have failed to respond adequately to conventional antiemetic treatments. However, the effects of Cesamet® have been reported to persist for a variable and unpredictable period of time following its oral administration; for example, adverse psychiatric reactions from using Cesamet® can persist for 48 to 72 hours following cessation of treatment.

CBD is another potent chemical derived from marijuana that is widely inhaled by patients from smoking the hemp leaves. To date, the FDA has only approved Epidiolex®, an oral solution (100 mg/ml) containing plant-derived CBD for the treatment of seizures associated with two rare and severe forms of epilepsy, Lennox-Gastaut syndrome and Dravet syndrome, in patients two years of age and older. CBD is a white to pale yellow crystalline solid. It is insoluble in water and is soluble in organic solvents. The primary medical applications of CBD are to combat severe and chronic pain, stress, depression, anxiety, cancer, epilepsy, schizophrenia, multiple sclerosis, migraine, arthritis, and the adverse effects of chemotherapy.

The presence of CBD can balance the agonistic activity of THC. THC activates the cannabinoid receptors CB1 and CB2 that are present in the brain and that are responsible for THC's psychoactive effects, while CBD suppresses the CB1 and CB2 receptors by operating as an indirect antagonist of cannabinoid agonists. Hence, CBD suppresses the activation of the CB1 and CB2 receptors by a cannabinoid like THC, creating a balanced effect.

When used in combination, THC and CBD have anti-inflammatory, appetite stimulant, anti-emetic, anti-convulsant, antioxidant, neuroprotective, and anti-tumoral actions. THC and CBD also can be used to combat epilepsy, depression, anxiety, schizophrenia, multiple sclerosis, migraine, and arthritis; and to alleviate the symptoms of cancer, AIDS, and spinal injuries; all of which improves quality of life for patients suffering from those debilitating conditions.

Further, THC and CBD are advantageous over other current prescription medications because they are non-habit forming, safe, and well-tolerated. Currently, about 2 million Americans have become dependent on or abused prescription pain pills because of the habit-forming nature of opioids. Additionally, opioids are associated with higher risk of overdose leading to death. There is a need in the art for a strong non-habit-forming painkiller as well as a well-tolerated and safe pain medication to prevent death from overdosing. Both THC and CBD are non-habit-forming strong painkillers that can replace opioids in treating severe and chronic pain.

In addition, the most prevalent mode of administration of medical cannabis is by smoking. Unfortunately, this mode of administration has adverse effects on the lungs. Cannabis smoke carries more tar and other particulate matter than tobacco, and may be a cause of lung diseases including lung cancer. Smoking may also negatively impact cannabinoids absorption. Studies show that the length of inhalation, hold time, and time between puffs attributed large inter-subject differences in plasma THC concentrations due to differences in the depth of inhalation, as participants titrated their THC dose. Moreover, many patients may find the act of smoking unappealing, as well as generally unhealthy.

Cannabinoids have been studied for delivery by other routes as well. European Patent No. 1361864 describes a formulation of cannabinoids as a buccal spray, but challenges associated with this delivery route include irritation of the mucosal membrane. Additional delivery methods developed to administer cannabinoids include the transdermal route as described in U.S. Pat. No. 6,328,992 and U.S. Patent Publication No. 2016/0022627. However, a bioactive material administered dermally can cause erratic effects and lower drug absorption into the system, and the use of permeation enhancers to improve drug absorption is likely toxic to the skin after chronic use. Other delivery systems include a propellant that provides a metered dose of cannabinoids, as described in U.S. Pat. Nos. 6,509,005 and 6,713,048; a pump-action spray as set forth in U.S. Pat. No. 6,946,150, intra-nasal delivery systems as discussed in U.S. Pat. Nos. 6,383,513 and 6,380,175; and oral solid lipid formulations composed by oral administration as described in U.S. Pat. No. 5,891,496.

Accordingly, there is a significant interest in developing other means to administer cannabis to patients.

There remains an unmet need in the art for a dosage form of THC and CBD, either individually or combined, for the treatment of multiple clinical conditions. A multiparticulate, immediate release dosage form as described below would allow for precise dosing, uniform drug delivery, targeted pharmacokinetics, minimized side effects, and convenience in administration.

SUMMARY OF THE INVENTION

The present invention provides multiparticulate solid oral dosage forms comprising one or more cannabinoids. The system may comprise particles (e.g., granules, particle agglomerates of any shape, beads, or pellets) having a size that may range from about 30 µm to about 1500 µm, or about 50 µm to about 1000 µm, in diameter, and with uniform loading. The multiparticulate solid oral dosage forms of the present invention may be formulated in a manner to provide immediate release of the one or more cannabinoids. The dosage forms of the present invention also may be formulated to achieve a targeted pharmacokinetic profile and to provide uniform distribution in the gastrointestinal tract.

The multiparticulate form can provide free flowing, precise dosing, and uniform drug loading, and may be compressed into tablets (regular tablets, orally-disintegrating tablets (ODT), self-disintegrated tablets, chewable tablets), filled into capsules (conventional hard gelatin capsules and easy open capsules to sprinkle) or loaded into stick packs to sprinkle over food or dissolve in water or other liquid drink.

One aspect of the current invention relates to a composition for the immediate release of one or more cannabinoids. In embodiments of the invention, the composition may comprise a population of particles, wherein each particle comprises: one or more cannabinoids, and one or more intra-granular excipients.

In some embodiments, the one or more cannabinoids may comprise THC, CBD, or a combination thereof.

In some embodiments, the one or more intra-granular excipients may comprise one or more diluents, binders, fillers, surfactants/emulsifying agents, disintegrating agents, or a combination thereof. In certain embodiments, the one or more intra-granular excipients may comprise one or more cellulose-derivative diluents. Examples of cellulose-derivative diluents may include lactose, isomalt, cellulose, starch, cyclodextrin, mannitol, and sorbitol.

In some embodiments, each particle may further comprise one or more surfactants/emulsifying agents.

In embodiments of the invention, the composition may comprise a population of particles, wherein each particle comprises one or more cannabinoids, and a porous bead core such as a mesoporous silica bead or a porous biodegradable glass bead. The particles may comprise a diameter of about 10 µm and 1000 µm. The ratio of pore volume to particle size may range from about 0.001 to about 0.8. Each particle may further comprise one or more surfactants/emulsifying agents.

The composition of the present invention may be provided in a dosage form such as a tablet (for example, an ODT, self-disintegrated tablet, or chewable tablet), capsule, or stick pack for oral administration. In some embodiments, the dosage form may comprise one or more extra-granular excipients, such as one or more fillers, binders, disintegrants, surfactants, lubricants, antioxidants, and/or flavors/sweeteners.

Another aspect of the invention relates to methods of preparing the immediate release compositions of the invention. In embodiments of the invention, the method of preparing a composition of particles comprising one or more cannabinoids and one or more intra-granular excipients may comprise combining the one or more cannabinoids with the one or more intra-granular excipients, and granulating the combination to produce immediate release particles. In embodiments of the invention, the method of preparing a composition of particles comprising one or more cannabinoids and porous bead cores may comprise loading the one or more cannabinoids onto porous bead cores.

In some embodiments, when the one or more cannabinoids are combined with the one or more intra-granular excipients and/or are loaded onto porous bead cores, the one or more cannabinoids may be in a granulating liquid. The granulating liquid may be an emulsion, a suspension, a hydroalcoholic mixture, or a combination thereof. The granulating liquid may comprise the one or more cannabinoids, one or more solubilizing agents and, in some embodiments, one or more surfactants/emulsifying agents. In some embodiments, the one or more solubilizing agents may be selected from an oil, glyceride, an alcohol, a hydroalcoholic solution, or a combination thereof. In certain embodiments, the one or more solubilizing agents may be an oil, such as cannabis oil or sesame oil. In certain embodiments, the one or more solubilizing agents may be a hydroalcoholic solution.

In some embodiments, the methods may further comprise preparing the granulating liquid comprising the one or more cannabinoids. The granulating liquid may be prepared by mixing the one or more cannabinoids with the one or more solubilizing agents. In certain embodiments, the granulating liquid may be prepared by mixing the one or more cannabinoids with the one or more solubilizing agents and with one or more surfactants/emulsifying agents.

In some embodiments, the combining of the one or more cannabinoids with the one or more intra-granular excipients occurs simultaneously, in whole or in part, with granulating the combination. In some embodiments, the combining of the one or more cannabinoids with the one or more intra-granular excipients occurs before granulating the combination.

In some embodiments, the granulation process may be a fluid bed granulation process, a wet granulation process, or a spray granulation process.

In some embodiments, the granulating liquid comprising the one or more cannabinoids is loaded onto the porous bead cores using a shear mixer.

In another aspect of the present invention, any of the embodiments of the composition for immediate release of one or more cannabinoids may be used in a method of treating a health issue in a subject in need thereof, wherein the health issue is selected from the group consisting of pain, nausea, sleep apnea, stress disorders, inflammation, depression, anxiety, epilepsy, schizophrenia, migraines, arthritis, weight loss, poor appetite, and a combination thereof. In some embodiments, the composition may be administered orally. In certain embodiments, prior to administration, the composition may be sprinkled on food or nutrient that is solid, semi-solid, or liquid; into water; or into other types of liquid drink.

BRIEF DESCRIPTION OF THE DRAWINGS

For a better understanding of the present invention, reference is made to the following description of an exemplary embodiment thereof, and the accompanying drawing, wherein:

FIGS. 8A-8C shows SEM images of THC and CBD particles at magnifications of 190× (FIG. 8A), 1600× (FIG. 8B), and 2200× (FIG. 8C). FIGS. 8D-8F shows blank porous bead cores at magnifications of 220× (FIG. 8D), 1000× (FIG. 8E), and 1600× (FIG. 8F).

DETAILED DESCRIPTION

Figure 1:
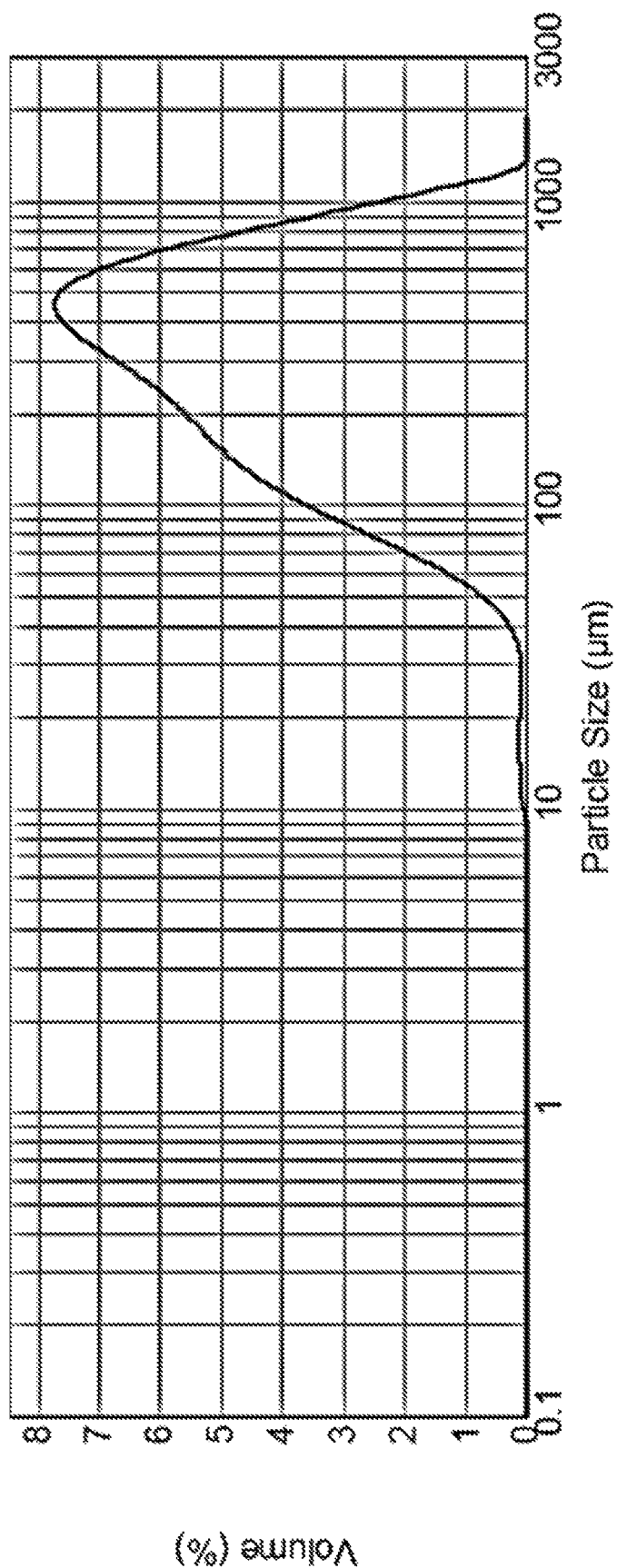
FIG. 1 shows the particle size distribution of both THC particles and CBD particles according to embodiments of the invention, as described in Example 1.

According to the present invention, multiparticulate, immediate release dosage forms are provided for administering one or more cannabinoids. In one aspect, the one or more cannabinoids comprise THC, CBD, or a combination thereof. In some embodiments, the one or more cannabinoids may be in an amount of about 1% to about 90% w/w. In certain embodiments, a final composition of THC and CBD, either individually or together, may range from about 1% to about 90% w/w.

In embodiments of the present invention, the compositions may comprise a population of particles, in which each particle comprises one or more cannabinoids, and one or more intra-granular excipients. In embodiments of the present invention, the compositions may comprise a population of particles, in which each particle comprises one or more cannabinoids and a porous bead core. The composition of the present invention may be provided in a dosage form such as a tablet (for example, regular tablet, ODT, self-disintegrated tablet, or chewable tablet), capsule, or stick pack.

Another aspect of the invention relates to methods of preparing the compositions of the present invention. In embodiments of the invention, compositions comprising particles that each comprise one or more cannabinoids and one or more intra-granular excipients may be prepared by a method comprising combining the one or more cannabinoids with the one or more intra-granular excipients, and granulating the combination to produce immediate release particles. In embodiments of the invention, compositions comprising particles that each comprise one or more cannabinoids and a porous bead core may be prepared by a method comprising loading the one or more cannabinoids onto porous bead cores.

In another aspect of the invention, the embodiments of the varying compositions of the present invention may be used in a method of treating a health issue in a subject in need thereof, wherein the health issue is selected from the group consisting of pain, nausea, sleep apnea, stress disorders, inflammation, depression, anxiety, epilepsy, schizophrenia, migraines, arthritis, weight loss, poor appetite, and a combination thereof. In one embodiment, the composition may be administered orally. In another embodiment, prior to administration, the composition may be sprinkled on food or nutrient that is solid, semi-solid, or liquid; into water; or into other types of liquid drink.

Compositions of the Present Invention

The compositions of the present invention comprise particles, in which each particle comprises one or more cannabinoids. The one or more cannabinoids may comprise THC, CBD, or a combination thereof. In certain embodiments, the one or more cannabinoids comprise both THC and CBD.

In embodiments of the invention, each particle of the composition may comprise the one or more cannabinoids, and one or more intra-granular excipients. The one or more intra-granular excipients may comprise one or more diluents, one or more binders, one or more fillers, one or more surfactants/emulsifying agents, one or more disintegrants, or a combination thereof. Diluents may serve different functions, such as to increase weight and improve content uniformity, improve cohesion, and/or promote flow. Examples of diluents include, but are not limited to, cellulose derivatives such as lactose, sucrose, isomalt, cellulose, starch, cyclodextrin, mannitol, microcrystalline cellulose, and sorbitol; calcium carbonate; plain or anhydrous calcium phosphate; calcium hydrogen phosphate dehydrate; calcium phosphate di- or tri-basic; magnesium carbonate; magnesium oxide; starch; sodium chloride; and a combination thereof.

Binders are excipients that may act as an adhesive to "bind together" particles and, in some cases, impart mechanical strength. In addition, binders can also provide volume to the composition. Examples of binders may include, but are not limited to, sugars such as sucrose, lactose, and glucose; corn syrup; soy polysaccharide; gelatin; povidone (e.g., Kollidon®, Plasdone®); Pullulan; cellulose derivatives such as microcrystalline cellulose, hydroxypropylmethyl cellulose (e.g., Methocel®), hydroxypropyl cellulose (e.g., Klucel®), ethylcellulose, hydroxyethyl cellulose, carboxymethylcellulose sodium, and methylcellulose; acrylic and methacrylic acid co-polymers; carbomer (e.g., Carbopol®); polyvinylpolypyrrolidine, polyethylene glycol)(Carbowax®); pharmaceutical glaze; alginates such as alginic acid and sodium alginate; gums such as acacia, guar gum, and arabic gums; tragacanth; dextrin and maltodextrin; milk derivatives such as whey; starches such as pregelatinized starch and starch paste; hydrogenated vegetable oil; magnesium aluminum silicate; and a combination thereof.

Fillers may increase the bulk of the composition and may make it easier to handle. Examples of fillers may include, but are not limited to, lactose, dextrose, saccharose, cellulose, starch, calcium phosphate, sucrose, dextrates, dextrin, maltodextrin, microcrystalline cellulose (e.g., PH102 or PH200, Avicel®), microfine cellulose, powdered cellulose, pregelatinized starch (e.g., Starch 1500®), calcium phosphate dihydrate, soy polysaccharide (e.g., Emcosoy®), gelatin, silicon dioxide, calcium sulfate, calcium carbonate, magnesium carbonate, magnesium oxide, sorbitol, mannitol, kaolin, polymethacrylates (e.g., Eudragit®), potassium chloride, sodium chloride, talc, and a combination thereof.

Surfactants/emulsifying agents can promote self-emulsification. Examples of surfactants/emulsifying agents may include, but are not limited to, sorbitan esters, ethoxylated sorbitan esters (Tween® 80; Sigma Aldrich, USA), ethoxylated linear alcohols, ethoxylated alkyl phenols, fatty acid esters, amine and amide derivatives, alkylpolyglucosides, ethyleneoxide/propylene oxide copolymers, polyalcohols and ethoxylated polyalcohols, thiols (e.g., mercaptans) and derivatives, poloxamers, polyethylene glycol-fatty acid esters, lecithins, and mixtures thereof. In certain embodiments, the surfactant/emulsifying agent may be selected from polysorbates (Tween® 80; Sigma Aldrich, USA), and polyethylene glycol esters of ricinoleic acid (Kolliphor® RH40, Kolliphor® EL; BASF, Germany).

Disintegrants may assist in breaking up the particles when exposed to an aqueous environment. Examples of disintegrants may include, but are not limited to, modified sodium starch glycolate, cross-linked povidone or crospovidone (e.g., Kollidon®), hydroxyl propyl cellulose, starch, alginic acid, sodium alginate, sodium carboxy-methylcellulose, croscarmellose sodium, carmellose sodium, microcrystalline cellulose, carboxystarch sodium, carboxymethyl starch sodium, potato starch, wheat starch, corn starch, rice starch, partly pregelatinized starch, hydroxypropyl starch, alginates, carbonates, and a combination thereof.

In embodiments of the invention, each particle of the composition may comprise one or more cannabinoids and a porous bead core. As used herein, the term "core" can refer to a carrier for the absorption and release of liquids, e.g., silica bead. In some embodiments of the invention, the core may comprise a silica bead, a biodegradable glass bead, or any other bead made of any compatible materials known in the art as suitable for oral administration (e.g., porous ceramics, porous calcium carbonate particles, porous zeolite particles, etc.).

The core may comprise one or more pores that extend from the surface of the core. The core may contain the one or more cannabinoids. According to some embodiments, the ratio of pore volume to particle size of the core may be between about 0.001 to about 0.8.

According to the present invention, the core is selected to achieve a free flowing multiparticulate system. According to some embodiments, the core may comprise mesoporous silica (e.g. Syloid® XDP 3150 (Grace, USA), Davisil® LC150A (Grace, USA), Neusilin® US2 (Fuji Chemicals, Japan)). Particle size, pore volume and specific surface area for the silica beads are given in Table 1 below.

TABLE 1

Physical properties of silica beads

| Physical properties | Syloid® XDP 3150 | Davisil® LC150A | Neusilin® US2 |
| --- | --- | --- | --- |
| Particle Size Distribution (μm) | 120-170 | 315-500 | 44-177 |
| Specific Surface Area (m²/g) | 320 | 340 | 300 |
| Pore Volume (ml/g) | 1.7 | 1.23 | 1.2 |
| Ratio of pore volume to particle size | 0.014 | 0.003 | 0.020 |
| Oil Adsorption Capacity (g/100 g) | 300 | — | 270-340 |
| Angle of Repose (°) | 36 | 36 | 30 |

The composition of the present invention may release a particular percentage of the one or more cannabinoids within a certain amount of time, as determined by dissolution testing. The dissolution test may be performed under the conditions summarized in Table 2 below.

TABLE 2

Conditions used for dissolution testing according to embodiments of the invention.

| Parameter | Condition |
| --- | --- |
| Apparatus | USP II (Paddle) |
| Paddle Speed | 100 rpm |
| Media | 1% Polysorbate 80 in DW |
| Media Volume | 500 ml |
| Temperature | 37° C. |
| Sampling Time Point(s) | 15, 30, 60, 240, 360, 720 min |

In some embodiments, the composition of the present invention may release about 30% or greater of the one or more cannabinoids over a period of about 30 minutes (0.5 hours) or less, or about 15 minutes (0.25 hours) or less, or about 10 minutes or less, from the start of the dissolution test. In some embodiments, the composition may release about 50% or greater of the one or more cannabinoids over a period of about 60 minutes (1 hour) or less, or about 30 minutes (0.5 hours) or less, or about 15 minutes (0.25 hours) or less, or about 10 minutes or less, from the start of the dissolution test. In some embodiments, the composition may release about 80% or greater of the one or more cannabinoids over a period of about 90 minutes (1.5 hours) or less, or about 60 minutes (1 hour), or less or about 30 minutes (0.5 hours) or less, or about 15 minutes (0.25 hours) or less, or about 10 minutes or less, from the start of the dissolution test.

The composition of the present invention may comprise particles having a particular size distribution. For example, in some embodiments, about 80% of the particles may between about 20 μm and about 2000 μm in diameter, or between about 30 μm and about 1000 μm in diameter, or between about 40 μm and about 900 μm in diameter. In some embodiments, about 80% of the particles may between about 2 μm and about 500 μm in diameter, or between about 4 μm and about 300 μm in diameter, or between about 5 μm and about 200 μm in diameter.

The composition of the present invention may be provided in a dosage form such as a tablet (e.g., ODT, self-disintegrating tablet, or chewable tablet), capsule, sprinkle, or stick pack. In some embodiments, the dosage form may comprise one or more extra-granular excipients, such as one or more fillers, one or more binders, one or more disintegrants, one or more lubricants, one or more antioxidants, one or more flavors/sweeteners, or a combination thereof.

Lubricants may reduce friction between granules and thus enhance followability, as well as prevent sticking to die wall in tablet compression and facilitate powder-filling in encapsulation. Lubricants may also assist with disintegration time and impact dissolution rate. Examples of lubricants may include, but are not limited to, calcium stearate, castor oil hydrogenated, glyceryl monostearate, glyceryl behenate, magnesium stearate, mineral oil, polyethylene glycol, polaxamer 407 or 188 or plain, sodium lauryl sulfate, sodium benzoate, stearic acid, sodium stearyl fumarate, silica, talc, and a combination thereof.

Antioxidants can have positive effects on the stability and efficacy of the composition. Examples of antioxidants may include, but are not limited to, acetylcysteine, ascorbyl palmitate, butylated hydroxyanisole (BHA), butylated hydroxytoluene (BHT), monothioglycerol, potassium nitrate, sodium ascorbate, sodium formaldehyde sulfoxylate, sodium metabisulfite, sodium bisulfite, vitamin E or a derivative thereof, propyl gallate, edetate (EDTA) (e.g., disodium edetate), diethylenetriaminepentaacetic acid (DTPA), triglycollamate (NT), and a combination thereof. Antioxidants may also comprise amino acids such as methionine, histidine, cysteine and those carrying a charged side chain, such as arginine, lysine, aspartic acid, and glutamic acid. Any stereoisomer (e.g., L-, D-, or a combination thereof) of any particular amino acid (e.g., methionine, histidine, arginine, lysine, isoleucine, aspartic acid, tryptophan, threonine and combinations thereof) or combinations of these stereoisomers, may be present so long as the amino acid is present either in its free base form or its salt form. For example, the L-stereoisomer may be used.

Flavors/sweeteners can help make the composition more palatable. Examples of flavors/sweeteners may include, but are not limited to, sugar, dextrose, fructose, aspartame, glycerin, mannitol, sucrose, saccharin sodium, acesulfame potassium, dextrates, liquid glucose, maltitol, saccharin, saccharin calcium; saccharin sodium, sodium cyclamate, sorbitol, stevia, syrup, xylitol, and a combination thereof.

Methods of Preparing the Compositions of the Invention

Methods of preparing the compositions of the present invention may comprise (a) combining one or more cannabinoids with one or more intra-granular excipients, and granulating the combination to produce immediate release particles; or (b) loading one or more cannabinoids onto porous bead cores.

The one or more cannabinoids that are combined with the one or more intra-granular excipients and/or that are loaded onto porous bead cores may be in a granulating liquid. The granulating liquid may be an emulsion, suspension, hydroalcoholic mixture, or a combination thereof. In some embodiments, the granulating liquid may comprise one or more solubilizing agents. The one or more solubilizing agents may be an oil, a glyceride, an alcohol, a hydroalcoholic solution, or a combination thereof. Examples of an oil may include, but are not limited to, sesame oil, cannabis oil, borage oil, coconut oil, cottonseed oil, soybean oil, safflower oil, sunflower oil, castor oil, corn oil, olive oil, palm oil, peanut oil, almond oil, rapeseed oil, peppermint oil, poppy seed oil, canola oil, palm kernel oil, hydrogenated soybean oil, hydrogenated vegetable oil, and a combination thereof. Examples of a glyceride may include, but are not limited to, a monoglyceride, diglyceride, triglyceride, and a combination thereof. Examples of an alcohol may include, but are not limited to, a monohydric alcohol, e.g., ethanol, methanol, or isopropyl alcohol. Examples of a hydroalcoholic mixture may include, but are not limited to, isopropyl alcohol mixed with water, or ethanol mixed with water, in varying ratios.

In some embodiments, the granulating liquid may further comprise one or more surfactants/emulsifying agents. Surfactants/emulsifying agents can promote self-emulsification. When an emulsion or suspension is formed, surface area expansion is created between the two phases. The emulsion or suspension is stabilized by the surfactant/emulsifying agent molecules that form a film around the internal phase droplet. In emulsion or suspension formation, the excess surface free energy is dependent on the droplet size and the interfacial tension. If the emulsion or suspension is not stabilized using surfactants/emulsifying agents, the two phases will separate reducing the interfacial tension and the free energy. Self-emulsifying drug delivery systems ("SEDDS") including self-micro-emulsifying drug delivery systems ("SMDDS") are mixtures of natural or synthetic oils, solid or liquid surfactants, or alternatively, one or more hydrophilic solvents and co-solvents/surfactants that have the ability to form oil-in-water emulsions or suspensions upon mild agitation followed by dilution in aqueous media, such as gastrointestinal fluids.

In some embodiments, the methods of the invention further comprise preparing the granulating liquid comprising the one or more cannabinoids. Preparation of the granulating liquid may involve mixing the one or more cannabinoids with the one or more solubilizing agents until the one or more cannabinoids are dissolved. In some embodiments, preparation of the granulating liquid may comprise mixing other components, such as one or more surfactants/emulsifying agents, with the one or more cannabinoids and the one or more solubilizing agents. The mixing of the contents may be by methods known in the art. For example, the contents may be mixed by simple mixing, or may be mixed with a mixing device continuously, periodically, or a combination thereof. Examples of mixing devices may include, but are not limited to, a magnetic stirrer, shaker, a paddle mixer, homogenizer, and any combination thereof.

In embodiments in which the particles comprise both THC and CBD, the THC and CBD may be in the same granulating liquid, or may be in different granulating liquids.

Combining One or More Cannabinoids with One or More Intra-Granular Excipients and Granulation In embodiments of the invention, the granulating liquid may be combined with one or more intra-granular excipients, and the combination may be granulated to produce immediate release particles. The combination of the granulating liquid may occur before granulation, or may occur concurrently in whole or in part with granulation.

In embodiments in which the particles comprise both THC and CBD, and in which the THC and CBD are in different granulating liquids, the granulating liquid may be combined together before combining with the one or more intra-granular excipients. Alternatively, the granulating liquid may be combined together simultaneously with combining with the one or more intra-granular excipients.

In some embodiments, the combination of the granulating liquid(s) with the one or more intra-granular excipients and granulation may be performed by a fluid bed granulation process. The one or more intra-granular excipients may be loaded into a granulator bowl of a fluid bed granulator and fluidized. The granulating liquid(s) may be added into the granulator bowl and onto the one or more intra-granular excipients. The addition of the granulating liquid(s) may be via a top spray, bottom spray, tangential spray, or an equivalent thereof. The parameters of this process, including the amount of pressure necessary to fluidize the one or more excipients in the granulator bowl, the inlet air temperature in the granulator bowl, the humidity level in the granulator bowl, the spray rate of the granulating liquid(s), and the fluid bed spray nozzle size and height, can all be determined by one of ordinary skill in the art. Examples of fluid bed granulators that may be used in these methods of the invention may include those manufactured by Glatt GMBH, Sainty International Group, GEA Group, Senieer, LB Bohle, Robert Bosch Packaging Technology GmbH, and SPX FLOW Danmark.

In some embodiments, the combination of the granulating liquid(s) with the one or more intra-granular excipients and granulation may be performed by a wet granulation process. In certain embodiments, the wet granulation process may be performed with a high-shear granulator. The one or more intra-granular excipients may be loaded into a bowl of a high-shear granulator and mixed at speeds ranging from about 25 rpm to about 1000 rpm, or about 100 rpm to about 500 rpm. The granulating liquid(s) may be added into the granulator bowl and onto the one or more intra-granular excipients, and the combination of the granulating liquid(s) and the one or more excipients is mixed under high shear at speeds ranging from about 500 rpm to about 5000 rpm, or about 1000 rpm to about 3000 rpm. The parameters of this process, such as the addition rate of the granulating liquid(s), can all be determined by one of ordinary skill in the art. In some embodiments, the high-shear granulator may be a vertical high-shear granulator. The vertical high-shear granulator may be top-driven or bottom-driven. In other embodiments, the high-shear granulator may be a horizontal high-shear granulator. Examples of high-shear granulators that may be used in these methods of the invention may include those manufactured by Glatt GMBH, SERVOLiFT LLC, Sainty International Group, GEA Group, Senieer, LB Bohle, and Robert Bosch Packaging Technology GmbH.

In certain embodiments, the wet granulation process may be performed with the Glatt CPS™ technology (Complex Perfect Spheres Technology). CPS™ is a patented technology by Glatt GMBH in which spherical granules are manufactured in two phases (i) nucleation of powders in which the solvent acts as a binder to create bridges between the particles of the active ingredient and a filler (e.g., microcrystalline cellulose), resulting in agglomeration; and (ii) spheronization of the granules due to centrifugal force exerted by the simultaneous spinning of the modified rotor disc to produce the smooth spherical granules/pellets. The CPS technology is disclosed in U.S. Pat. No. 6,354,728 and PCT Publication No. WO04052607, which are incorporated herein by reference. The one or more intra-granular excipients may be loaded into a bowl and the granulating liquid(s) may be added into the bowl and onto the one or more excipients.

In certain embodiments, the wet granulation process may be performed by extrusion-spheronization. The one or more intra-granular excipients may be loaded into a bowl and the granulating liquid(s) may be added into the bowl and onto the one or more intra-granular excipients. The combination of the granulating liquid(s) and the one or more excipients may be mixed, such as with a planetary mixer, a high-shear mixer as described above, or a sigma blade mixer. The combination mixture may then undergo extrusion, in which pressure is applied to the combination mixture until it flows out through one or more orifices to produce the extrudates. Extrusion may be performed using a screw extruder, which uses a screw to develop the necessary pressure to force the combination mixture to flow through the one or more orifices; sieve extruder, which uses a rotating or oscillating arm to press the combination mixture through a sieve; basket extruder, which uses a rotating or oscillating arm to press the combination mixture through a sieve that is part of a vertical cylindrical wall; roll extruder, in which the combination mixture is fed between a roller and a perforated plate or ring due; ram extruder, in which the combination mixture compressed and forced through one or more orifices by a piston that is inside a cylinder or channel; or other types of extruders known in the art. The extruded combination mixture may then undergo spheronization, in which the mixture is broken into uniform lengths and are gradually transformed into spherical shapes. The parameters of the extrusion-spheronization process can be determined by one of ordinary skill in the art. Examples of extrusion-spheronization equipment that may be used in these methods of the invention may include those manufactured by Glatt GMBH, Sainty International Group, GEA Group, LB Bohle, and Robert Bosch Packaging Technology GmbH.

In certain embodiments, the wet granulation process may be performed with a connection mixer, roller compactor, or "V" blender, using methods known in the art.

Following wet granulation, the particles may be dried using methods known in the art, for example, using a fluid bed processor.

In some embodiments, the combination of the granulating liquid(s) with the one or more intra-granular excipients and granulation may be performed by a spray granulation process. The granulating liquid(s), which includes one or more surfactants as described above, is mixed well with the one or more intra-granular excipients, resulting in a dispersion. This dispersion may comprise about 5% to about 90% of solid content. The dispersion is then sprayed onto a fluidized or spouted bed to produce particles. The parameters of this process can be determined by one of ordinary skill in the art. Examples of spray granulators that may be used in these methods of the invention may include those manufactured by Glatt GMBH, GEA Group, LB Bohle, Robert Bosch Packaging Technology GmbH, and Allgaier Werke GmbH.

In certain embodiments, the spray granulation process may be performed using Procell® sprouted bed technology. The Procell technology is disclosed in U.S. Pat. Nos. 7,993, 595 and 8,597,685, and in European Patent Nos. 1125629 and 1325775, which are all incorporated herein by reference.

Loading One or More Cannabinoids onto Porous Bead Cores

In embodiments of the invention, the granulating liquid(s) comprising the one or more cannabinoids may be loaded onto porous bead cores. The granulating liquid(s) may be loaded onto the porous bead cores by mixing the granulating liquid(s) with the cores. In certain embodiments, a high shear granulator may be used to mix the granulating liquid (s) with the porous bead cores. In some embodiments, the mixing may occur until a free-flowing powder mixture is produced. Thereafter, a composition according to the present invention is formed.

Preparing the Dosage Forms

According to embodiments of the invention, the particles comprising the one or more cannabinoids prepared by the methods described above may be sized, milled, and screened according to methods known in the art. The particles may be blended with extra-granular excipients as described above, and the resulting blend may be processed into a dosage form such as a tablet, capsule, or stick pack using conventional methodologies.

Methods of Use of the Composition of the Invention

An aspect of the invention relates to methods of treating a health issue in a subject in need thereof, wherein the methods comprise administering an immediate release composition of the invention.

The present invention also relates to the use of an immediate release composition of the invention for treating a health issue in a subject in need thereof. The use may comprise administering the composition to the subject.

The present invention relates to the use of an immediate release composition of the invention in the manufacture of a medicament for treating a health issue in a subject in need thereof.

The present invention further relates to an immediate release composition of the invention for use in treating a health issue in a subject in need thereof. The use may comprise administering the composition to the subject.

The health issue may be selected from the group consisting of pain, nausea, sleep apnea, stress disorders, inflammation, depression, anxiety, epilepsy, schizophrenia, migraines, arthritis, weight loss, poor appetite, and a combination thereof.

In some embodiments, the composition may be administered orally.

In some embodiments, prior to administration, the composition may be sprinkled on food or nutrient that is solid, semi-solid, or liquid; into water; or into other types of liquid drink.

EXAMPLES

Example 1

A study was performed to prepare and assess a composition according to embodiments of the invention, in which the composition comprises both particles that comprise THC and particles that comprise CBD, as shown in Table 3 below. The particles were prepared using the top spray fluid bed granulation process according to embodiments of the invention.

TABLE 3

Composition of Example 1.

| | Component | Function | % of Total Weight |
|---|---|---|---|
| Granulating liquid | THC (20% Dronabinol in Ethanol) | Active in solubilizing agent | 5.54 |
| | Kolliphor ® EL | Surfactant/ emulsifying agent | 0.2 |
| Granulating liquid | CBD | Active | 11.08 |
| | Sesame oil | Solubilizing agent | 8.6 |
| | Polysorbate 80 | Surfactant/ emulsifying agent | 6 |
| Intra-granular Excipient | Pharmatose ® 200M (EU) (Milled Lactose Monohydrate) | Diluent | 45.28 |

TABLE 3-continued

Composition of Example 1.

| | Component | Function | % of Total Weight |
|---|---|---|---|
| | Kollidon ® 30 | Binder | 3 |
| | Vivapur ® 101 (Microcrystalline Cellulose) | Disintegrant | 20.3 |
| Granulation Process | Methanol | Processing solvent | Non-residual |
| | Purified water | Processing solvent | Non-residual |
| | TOTAL | | 100 |

The particle size distribution of the composition, shown in FIG. 1, was obtained using dynamic light scattering technique (Malvern Instruments, USA). As shown in the figure, over 70% of the particles are between about 100 µm and about 700 µm in diameter.

Figure 2A:
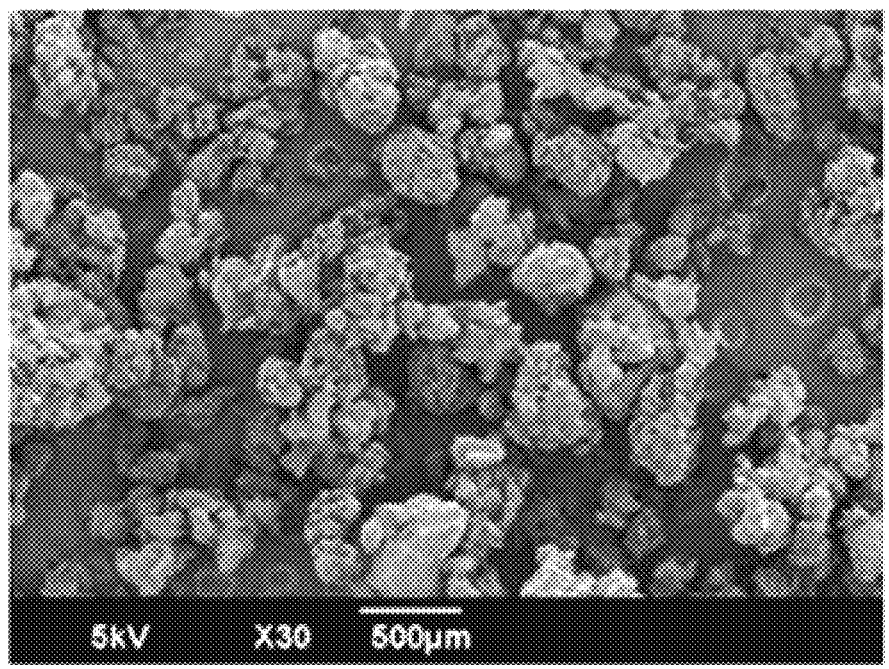
FIGS. 2A and 2B shows scanning electron microscopic (SEM) images at magnifications of 30× (FIG. 2A) and 75× (FIG. 2B) of THC particles and CBD particles according to embodiments of the invention, as described in Example 1.
Figure 2B:
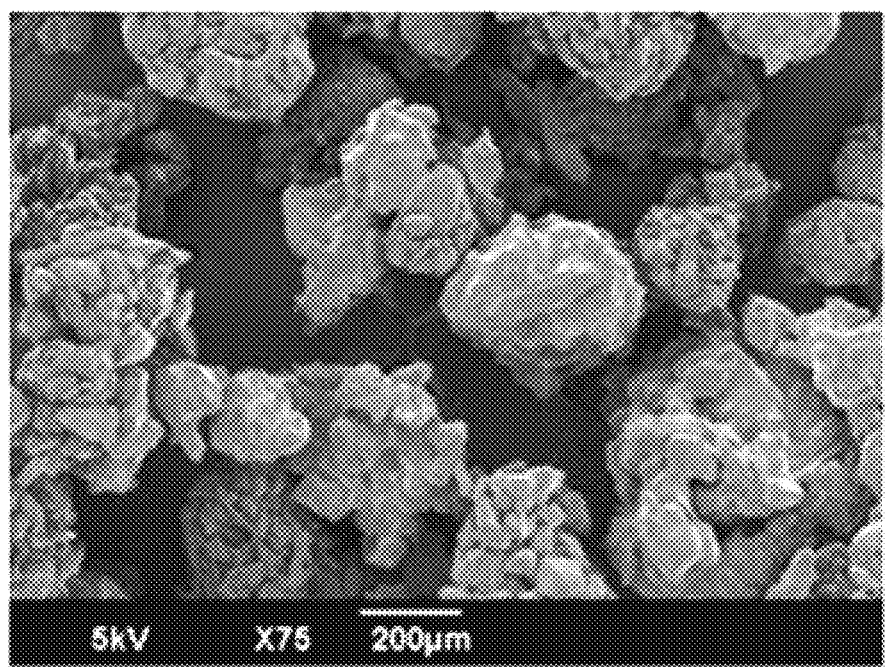

SEM images of the granules obtained using obtained using Electronic Scanning Microscopy Imaging technique are shown in FIGS. 2A and 2B.

A dissolution test was performed using purified water, USP, as the dissolution medium in a dissolution volume of 900 ml. A USP Type II paddle apparatus was used to mix the dissolution medium at a paddle speed of 75 rpm. The bath temperature was 37° C., and a 10-µm porous filter was used to sample aliquots.

Figure 3:
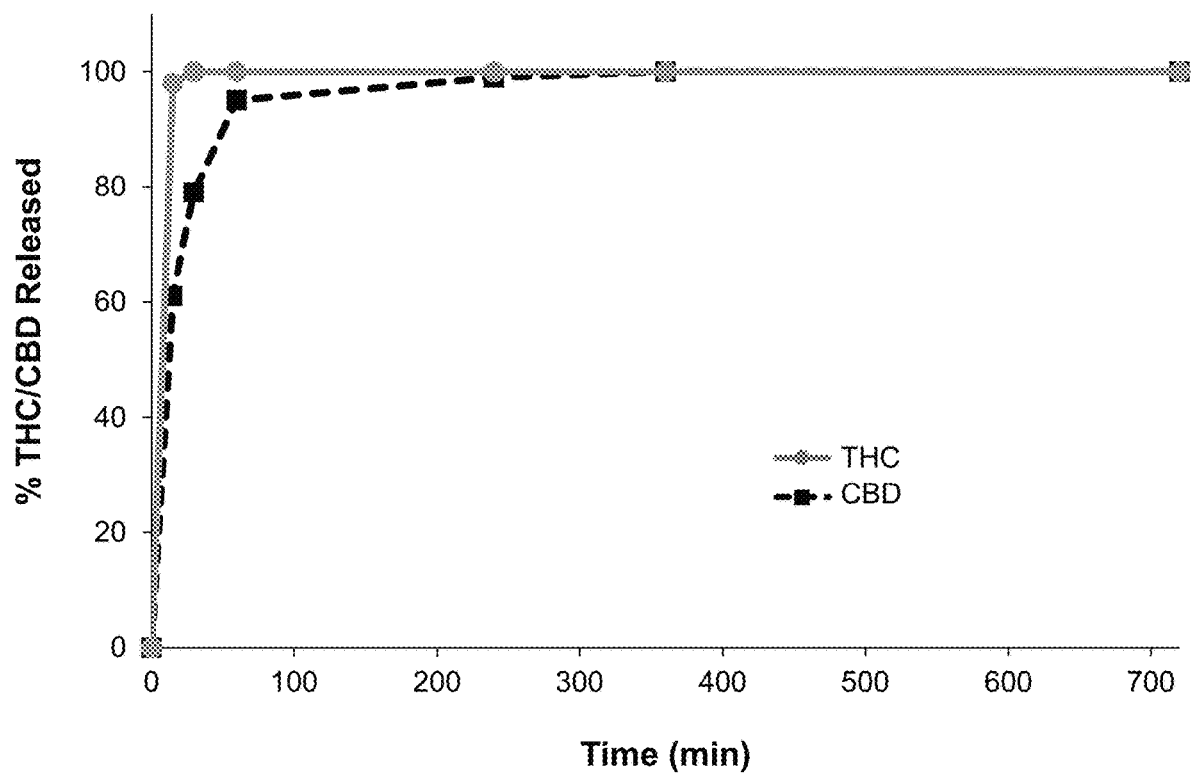
FIG. 3 shows the dissolution profile of both THC particles and CBD particles according to embodiments of the invention, as described in Example 1.

The resulting dissolution profiles for both the THC particles and the CBD particles are shown in FIG. 3. Dissolution of both the THC particles and CBD particles exhibited an immediate release dissolution profile.

Example 2

A study was performed to prepare and assess a composition according to embodiments of the invention, in which the composition comprises both particles that comprise THC and particles that comprise CBD, as shown in Table 4 below. The particles were prepared using the high-shear granulation process with the CPS technology according to embodiments of the invention.

TABLE 4

Composition of Example 2.

| | Component | Function | % of Total Weight |
|---|---|---|---|
| Granulating liquid | THC (20% Dronabinol in Ethanol) | Active in solubilizing agent | 5.54 |
| | Kolliphor ® EL | Surfactant/ emulsifying agent | 0.2 |
| Granulating liquid | CBD | Active | 11.08 |
| | Sesame oil | Solubilizing agent | 8.6 |
| | Polysorbate 80 | Surfactant/ emulsifying agent | 6 |
| Intra-granular Excipient | Pharmatose ® 200M (EU) (Milled Lactose Monohydrate) | Diluent | 45.28 |
| | Kollidon ® 30 | Binder | 3 |
| | Vivapur ® 101 (Microcrystalline Cellulose) | Disintegrant | 20.3 |

TABLE 4-continued

Composition of Example 2.

| | Component | Function | % of Total Weight |
|---|---|---|---|
| Granulation Process | Methanol | Processing solvent | Non-residual |
| | Purified water | Processing solvent | Non-residual |
| | TOTAL | | 100 |

Figure 4:
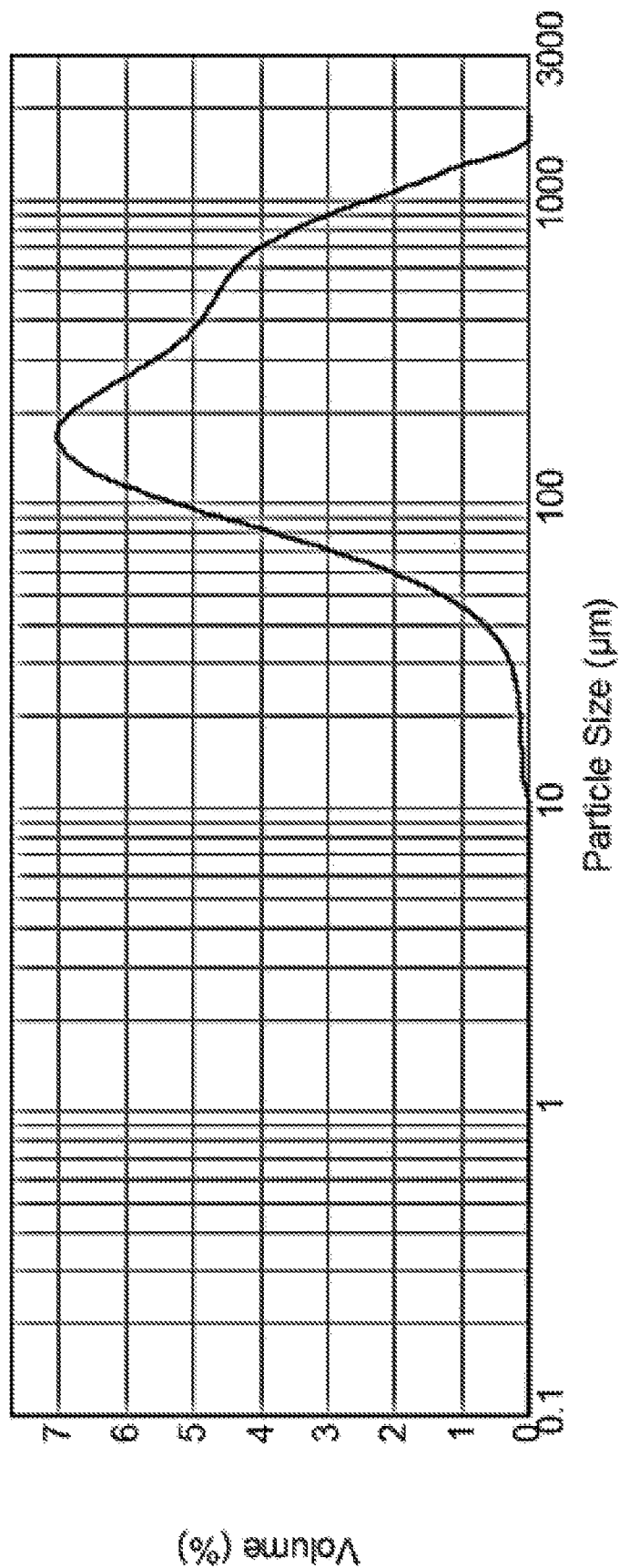
FIG. 4 shows the particle size distribution of both THC particles and CBD particles according to embodiments of the invention, as described in Example 2.

The particle size distribution of the composition, shown in FIG. 4, was obtained using dynamic light scattering technique (Malvern Instruments, USA). As shown in the figure, over 70% of the particles are between about 80 µm and about 700 µm in diameter.

Figure 5A:
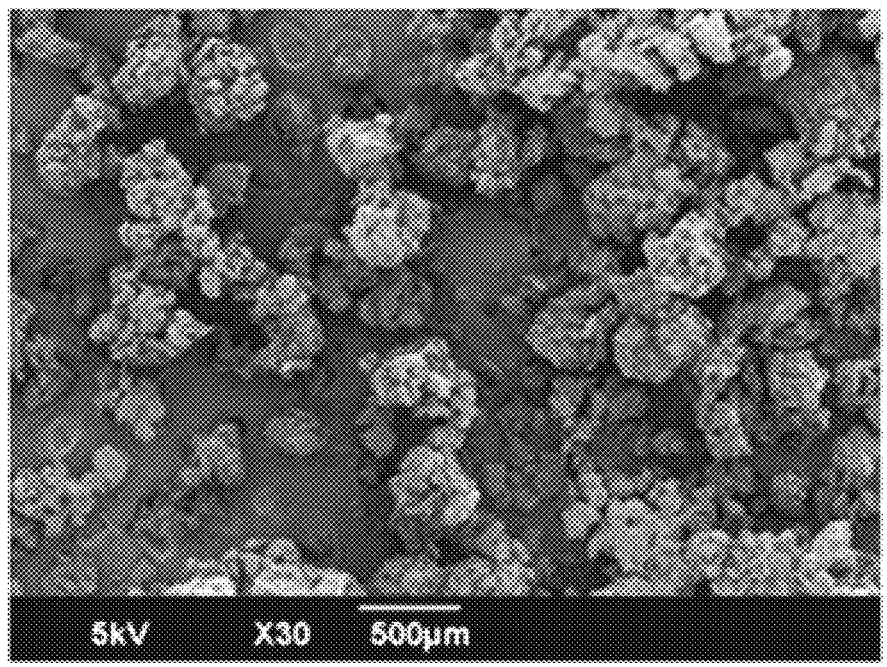
FIGS. 5A and 5B shows SEM images at magnifications of 30× (FIG. 5A) and 75× (FIG. 5B) of THC particles and CBD particles according to embodiments of the invention, as described in Example 2.
Figure 5B:
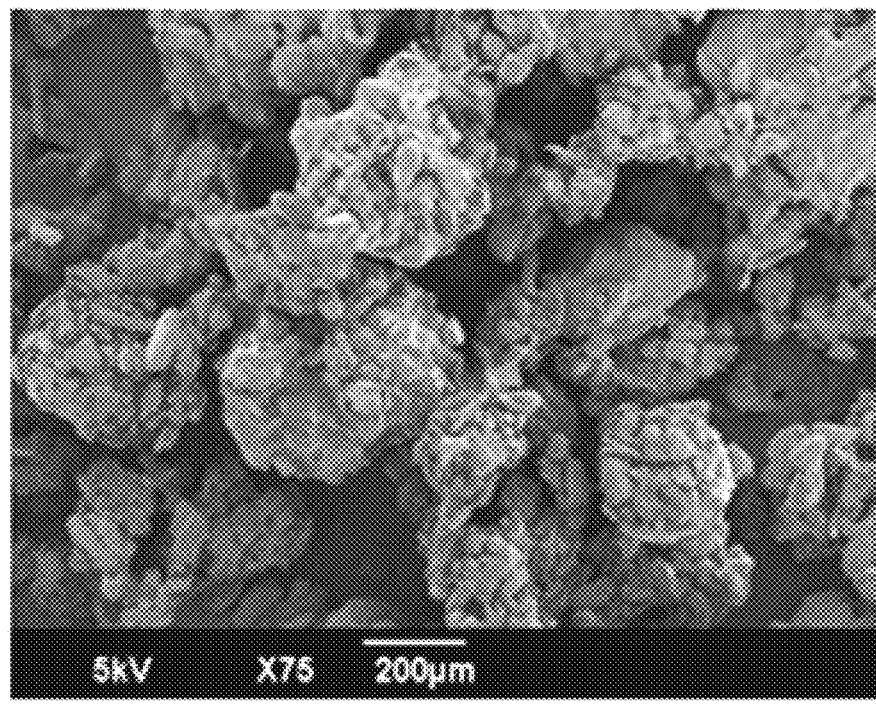

SEM images of the granules obtained using Electronic Scanning Microscopy Imaging technique are shown in FIGS. 5A and 5B.

A dissolution test was performed using 1% polysorbate 80 in distilled water as the dissolution medium in a dissolution volume of 500 ml. A USP Type II paddle apparatus was used to mix the dissolution medium at a paddle speed of 100 rpm. The bath temperature was 37° C.

Figure 6:
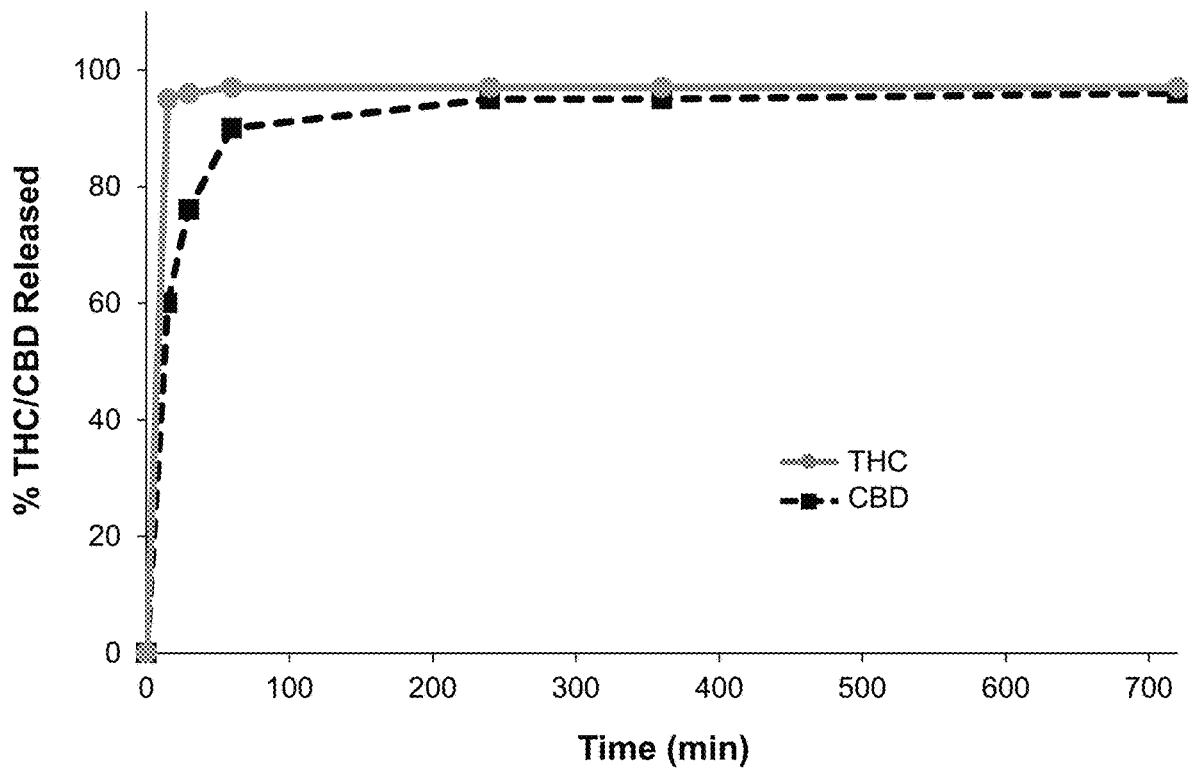
FIG. 6 shows the dissolution profile of both THC particles and CBD particles according to embodiments of the invention, as described in Example 3.

The resulting dissolution profiles for both the THC particles and the CBD particles are shown in FIG. 6. Dissolution of both the THC particles and CBD particles exhibited an immediate release dissolution profile.

Example 3

A study was performed to prepare and assess a composition according to embodiments of the invention, in which the composition comprises both particles that comprise THC and particles that comprise CBD, as shown in Table 5 below. The particles were prepared by loading the THC and CBD onto porous bead cores according to embodiments of the invention.

TABLE 5

Composition of Example 3.

| Component | Function | % of Total Weight |
|---|---|---|
| THC in sesame oil | Active in solubilizing agent | 14 |
| CBD | Active | 1.4 |
| Tween ® 80 | Surfactant/emulsifying agent | 51.6 |
| Neusilin ® US2 (Silica) | Porous bead core | 33 |
| | Total | 100 |

Figure 7A:
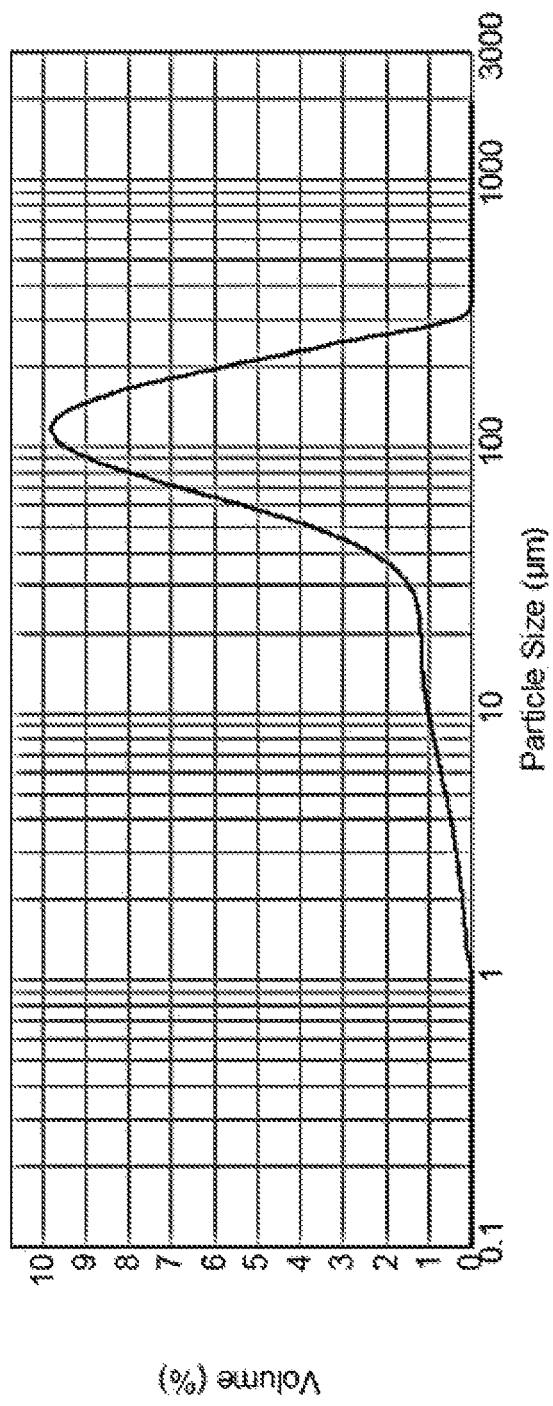
FIG. 7A shows the particle size distribution of both THC particles and CBD particles according to embodiments of the invention.
Figure 7B:
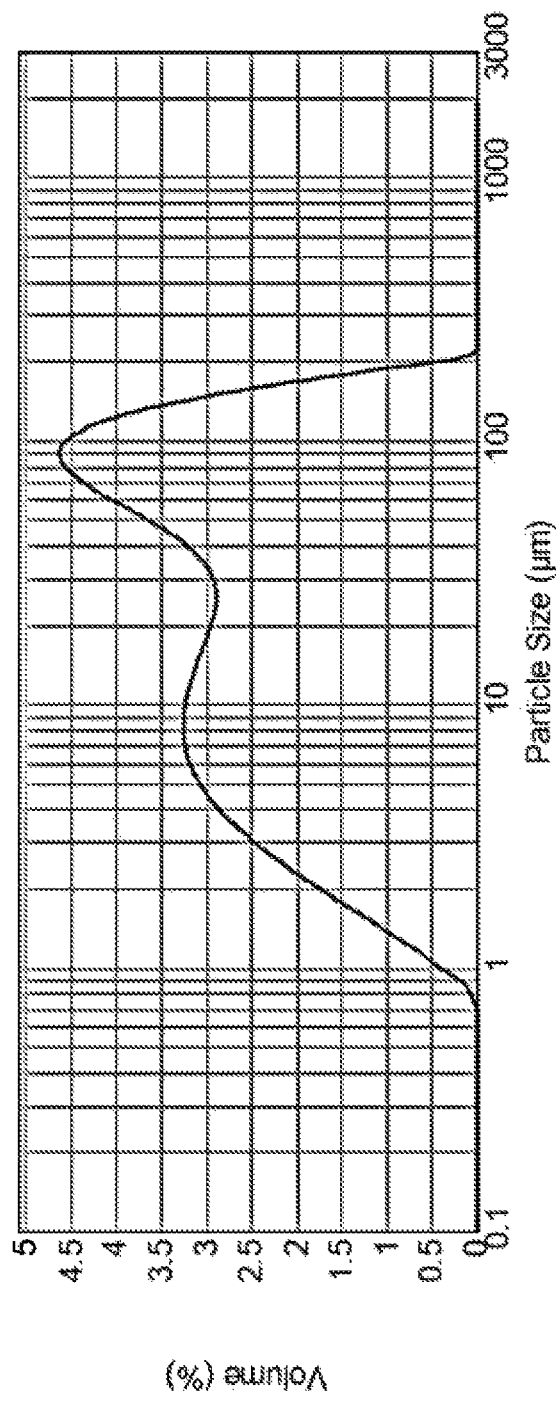
FIG. 7B shows the particle size distribution of blank porous bead cores, as described in Example 3.
Figure 8A:
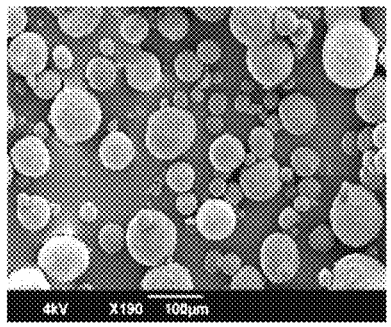
FIGS. 8A-8F shows SEM images of THC and CBD particles and blank porous bead cores particles according to embodiments of the invention, as described in Example 3.
Figure 8B:
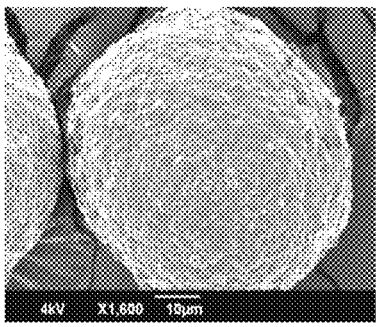
Figure 8C:
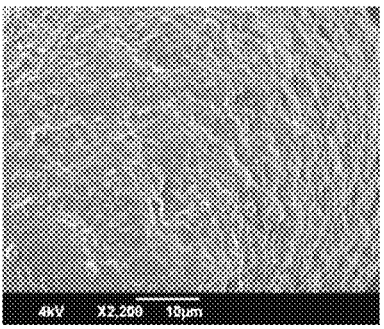
Figure 8D:
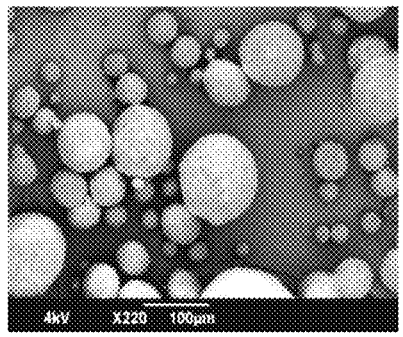
Figure 8E:
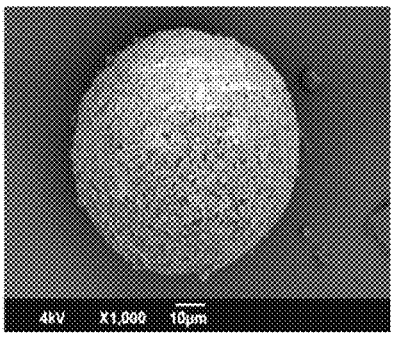
Figure 8F:
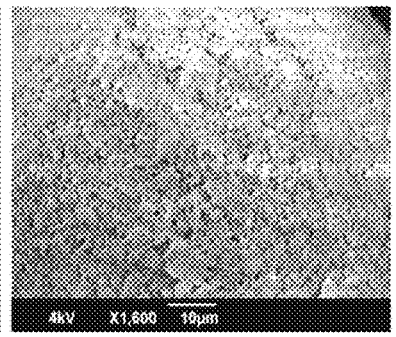

Particle size distribution was obtained using dynamic light scattering technique (Malvern Instruments, USA) for the composition as well as for blank porous bead cores. As shown in FIGS. 7A and 7B, over 70% of the particles of the composition are between about 20 µm and about 200 µm in diameter (FIG. 7A), while over 70% of the particles of the blank porous bead cores are between about 2 µm and about 100 µm in diameter (FIG. 7B).

SEM images of the granules obtained using Electronic Scanning Microscopy Imaging technique are shown in FIGS. 8A-8F.

A dissolution test was performed using 1% polysorbate 80 in distilled water as the dissolution medium in a dissolution volume of 500 ml. A USP Type II paddle apparatus was used to mix the dissolution medium at a paddle speed of 100 rpm. The bath temperature was 37° C.

Figure 9:
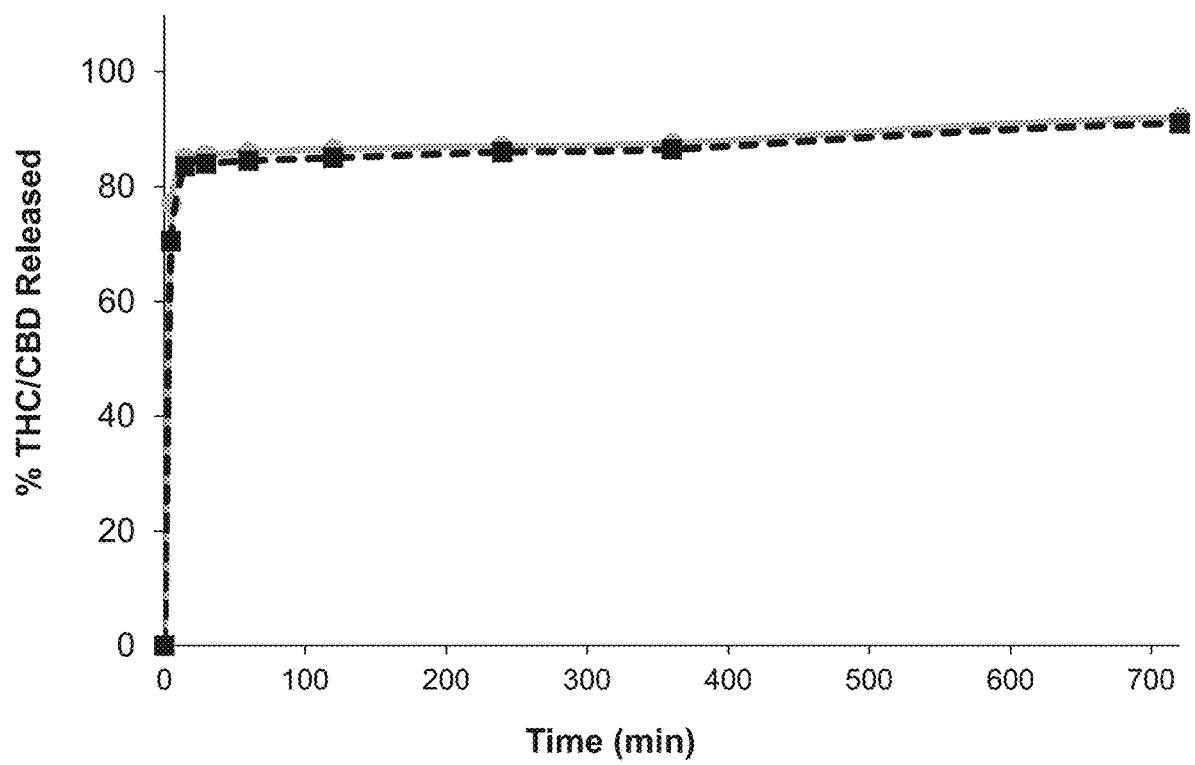
FIG. 9 shows the dissolution profile of both THC particles and CBD particles according to embodiments of the invention, as described in Example 3.

The resulting dissolution profiles for both the THC particles and the CBD particles are shown in FIG. 9. The dissolution profile of the THC particles was nearly the same as the dissolution profile of the CBD particles, and both particles achieved 80% release in less than 20 minutes.

Although specific embodiments of the present invention have been disclosed herein, those having ordinary skill in the art will understand that changes can be made to the specific embodiments without departing from the spirit of the invention. The scope of the invention is not to be restricted, therefore, to the specific embodiments. Furthermore, it is intended that the appended claims cover any and all such applications, modifications, and embodiments within the scope of the present invention.

What is claimed is:

1. A composition for immediate release of one or more cannabinoids, the composition comprising a population of particles, wherein each particle comprises:
   (a) the one or more cannabinoids;
   (b) one or more intra-granule excipients;
   wherein about 80% of the particles is between about 20 µm and about 2000 µm in diameter; and
   wherein the composition releases at least about 30% of the one or more cannabinoids over a period of about 30 minutes or less.

2. The composition of claim 1, wherein the one or more cannabinoids comprises Δ9-tetrahydrocannabinol (THC), cannabidiol (CBD), or a combination thereof.

3. The composition of claim 1, wherein the one or more cannabinoids comprises a combination of THC and CBD.

4. The composition of claim 1, wherein the one or more intra-granule excipients comprises one or more diluents, one or more binders, one or more fillers, one or more surfactants/emulsifying agents, one or more disintegrants, or a combination thereof.

5. The composition of claim 1, wherein the one or more intra-granule excipients comprises one or more cellulose derivatives.

6. The composition of claim 5, wherein the one or more cellulose derivatives is selected from the group consisting of lactose, isomalt, cellulose, starch, cyclodextrin, mannitol, sorbitol, and a combination thereof.

7. The composition of claim 1, wherein the composition releases about 30% of the one or more cannabinoids over a period of about 30 minutes or less.

8. The composition of claim 1, wherein about 70% of the particles is between about 100 µm and about 700 µm in diameter.

* * * * *